(12) United States Patent
Tanaka et al.

(10) Patent No.: US 9,431,348 B2
(45) Date of Patent: Aug. 30, 2016

(54) SEMICONDUCTOR DEVICE MANUFACTURING METHOD AND MANUFACTURING DEVICE FOR MARKING A CRYSTAL DEFECT

(71) Applicant: FUJI ELECTRIC CO., LTD., Kawasaki-shi (JP)

(72) Inventors: Atsushi Tanaka, Tsukuba (JP); Takashi Tsuji, Tsukuba (JP)

(73) Assignee: FUJI ELECTRIC CO., LTD., Kawasaki-shi (JP)

( * ) Notice: Subject to any disclaimer, the term of this patent is extended or adjusted under 35 U.S.C. 154(b) by 0 days.

(21) Appl. No.: 14/505,589

(22) Filed: Oct. 3, 2014

(65) Prior Publication Data
US 2015/0024520 A1 Jan. 22, 2015

Related U.S. Application Data

(63) Continuation of application No. PCT/JP2013/057737, filed on Mar. 18, 2013.

(30) Foreign Application Priority Data

Apr. 27, 2012 (JP) ................................. 2012-104222

(51) Int. Cl.
*H01L 23/544* (2006.01)
*H01L 21/66* (2006.01)
*G01N 21/95* (2006.01)
(Continued)

(52) U.S. Cl.
CPC ......... *H01L 23/544* (2013.01); *G01N 21/9501* (2013.01); *H01L 21/67282* (2013.01); *H01L 21/67288* (2013.01); *H01L 22/12* (2013.01); *H01L 29/1608* (2013.01); *H01L 29/2003* (2013.01); *H01L 2223/5442* (2013.01); *H01L 2223/54426* (2013.01);
(Continued)

(58) Field of Classification Search
None
See application file for complete search history.

(56) References Cited

U.S. PATENT DOCUMENTS 4,958,373 A * 9/1990 Usami et al. .................. 382/149
5,633,173 A * 5/1997 Bae ................................ 438/16
(Continued)

FOREIGN PATENT DOCUMENTS

CN 1979342 A 6/2007
CN 103311146 A 9/2013
(Continued)

OTHER PUBLICATIONS
International Search Report issued in PCT/JP2013/057737, mailing dated Jun. 4, 2013. English translation provided.
(Continued)

*Primary Examiner* — Scott B Geyer
(74) *Attorney, Agent, or Firm* — Rossi, Kimms & McDowell LLP

(57) ABSTRACT

A marker which is a reference of a coordinate position defining a region of a chip that is manufactured in a semiconductor substrate is formed. A crystal defect on the semiconductor substrate is detected. The coordinate position of the detected crystal defect is detected on the basis of the marker. Therefore, it is possible to detect the position of a semiconductor chip including the crystal defect among the semiconductor chips manufactured on the semiconductor substrate. As a result, it is possible to easily detect the position of the semiconductor device including the position of the crystal defect on the semiconductor substrate.

10 Claims, 2 Drawing Sheets

(51) Int. Cl.
  *H01L 21/67* (2006.01)
  *H01L 29/16* (2006.01)
  *H01L 29/20* (2006.01)

(52) U.S. Cl.
  CPC ............... *H01L 2223/54433* (2013.01); *H01L 2223/54453* (2013.01); *H01L 2924/0002* (2013.01)

(56) References Cited

U.S. PATENT DOCUMENTS

| | | | | |
|---|---|---|---|---|
| 5,699,153 | A | * | 12/1997 | Takamoto et al. ......... 356/237.1 |
| 5,847,821 | A | * | 12/1998 | Tracy et al. ............... 356/237.1 |
| 5,877,035 | A | * | 3/1999 | Fujino et al. .................... 438/16 |
| 6,122,562 | A | * | 9/2000 | Kinney et al. ................ 700/121 |
| 6,157,444 | A | * | 12/2000 | Tomita et al. ............. 356/237.1 |
| 6,320,655 | B1 | * | 11/2001 | Matsushita et al. ........ 356/237.2 |
| 6,559,457 | B1 | * | 5/2003 | Phan et al. .................. 250/491.1 |
| 6,603,540 | B1 | * | 8/2003 | Kaupp ........................ 356/237.1 |
| 6,760,472 | B1 | * | 7/2004 | Takeda ............... G06K 7/10544 235/380 |
| 6,934,920 | B2 | * | 8/2005 | Fujii ....................... H01L 22/20 257/E21.525 |
| 7,314,766 | B2 | * | 1/2008 | Sugamoto ............... H01L 22/24 257/E21.527 |
| 8,817,251 | B2 | | 8/2014 | Tsuchiya |
| 2007/0081150 | A1 | * | 4/2007 | Leonard et al. ........... 356/237.2 |
| 2007/0134598 | A1 | | 6/2007 | Iwamoto |
| 2008/0246959 | A1 | * | 10/2008 | Toda ....................... H01L 22/22 356/237.5 |
| 2009/0161097 | A1 | * | 6/2009 | Friedrich et al. .......... 356/237.5 |
| 2011/0229011 | A1 | * | 9/2011 | Yanai ............................ 382/145 |
| 2011/0231129 | A1 | * | 9/2011 | Yanai .............................. 702/81 |
| 2013/0235373 | A1 | * | 9/2013 | Tsuchiya .................... 356/237.5 |

FOREIGN PATENT DOCUMENTS

| | | |
|---|---|---|
| JP | 2000124271 A | 4/2000 |
| JP | 2001345357 A | 12/2001 |
| JP | 2007318029 A | 12/2007 |
| JP | 2007318030 A | 12/2007 |
| JP | 2007318031 A | 12/2007 |

OTHER PUBLICATIONS

Office Action issued in Chinese Appln. No. 201380018848.0 mailed Feb. 1, 2016. English translation provided.

* cited by examiner

SEMICONDUCTOR DEVICE MANUFACTURING METHOD AND MANUFACTURING DEVICE FOR MARKING A CRYSTAL DEFECT

BACKGROUND OF THE INVENTION

A. Field of the Invention

The present invention relates to a semiconductor device manufacturing method and a semiconductor device manufacturing device which can detect the position of a crystal defect with ease.

B. Description of the Related Art

Silicon carbide (SiC) is expected to be used as the next-generation semiconductor material. A semiconductor element made of SiC is characterized in that the resistance (on resistance) thereof in an on state can be reduced to a few hundredths of that of an element made of silicon (Si) and the semiconductor element can be used under a high-temperature environment of 200° C. or more.

SiC has a material advantage over other semiconductor materials. That is, SiC is characterized in that 4H-SiC has a band gap of 3.25 eV that is about three times more than the band gap, 1.12 eV, of Si and SiC has an electric field intensity of 2 mV/cm to 4 mV/cm that is about one digit greater than that of Si. SiC is experimentally used to manufacture various types of devices including rectifying devices, such as diodes, and switching devices, such as transistors and thyristors.

However, there are various crystal defects or dislocations in the SiC substrate. When an epitaxial film is formed on the SiC substrate, the number of crystal defects tends to increase. In a silicon carbide semiconductor device, such as a Schottky diode which is formed using the SiC substrate, the crystal defect causes a reduction in breakdown voltage or an increase in leakage current.

Therefore, it is necessary to acquire information about the position of the crystal defects in the plane of a wafer or the type of defects before a semiconductor device is manufactured using the SiC substrate. An inspection device satisfying the necessity has been proposed (for example, see JP 2007-318029A, JP 2007-318030A and JP 2007-318031A). JP 2007-318029A and JP 2007-318030A disclose a technique which inspects the distribution of crystal defects using an electroluminescence method. JP 2007-318031A discloses a technique which radiates excitation light to a measurement position or applies a voltage to emit light thereto and detects the emitted light at a plurality of measurement positions to map the position of the crystal defect.

However, in the above-mentioned methods, a very small deviation in the position of the detected defect occurs in each measurement operation, depending on the shape of the SiC substrate or the position of the SiC substrate relative to the inspection device. Therefore, when the semiconductor substrate is divided in a semiconductor device manufacturing process, it is difficult to easily determine the position of a semiconductor device including the crystal defect, even though an inspection device is used.

The invention has been made in view of the above-mentioned problems and provides a technique that can easily detect the position of a semiconductor device including the position of a crystal defect on a semiconductor substrate.

SUMMARY OF THE INVENTION

A semiconductor device manufacturing method according to an aspect of the invention has the following characteristics. A step of forming a marker which is a reference of a coordinate position defining a region of a chip that is manufactured in a semiconductor substrate is performed. Then, a step of detecting a crystal defect on the semiconductor substrate and a step of detecting the coordinate position of the detected crystal defect on the basis of the marker are performed.

The semiconductor device manufacturing method may further include a step of, when a plurality of semiconductor devices are manufactured on the semiconductor substrate, detecting a semiconductor device including the crystal defect among the plurality of the semiconductor devices, on the basis of the coordinate position.

The marker may be formed at the same time as the crystal defect is detected.

The marker may be formed after the crystal defect is detected.

The semiconductor substrate may be made of silicon carbide.

The semiconductor substrate may be made of gallium nitride.

The marker may be formed by laser.

The marker may be formed by photolithography.

The marker may be formed by physical cutting.

Light may be radiated to the semiconductor substrate and the crystal defect may be detected on the basis of the diffusion, reflection, and transmission of the radiated light.

A semiconductor device manufacturing device according to another aspect of the invention includes a marker forming unit that forms a marker which is a reference of a coordinate position defining a region of a chip that is manufactured in a semiconductor substrate and an inspection unit that detects a crystal defect on the semiconductor substrate. The inspection unit detects the coordinate position of the detected crystal defect on the basis of the marker.

According to the above-mentioned structure, the marker which is a reference is formed on the semiconductor substrate. When the crystal defect on the semiconductor substrate is detected, the coordinate position of the detected crystal defect is detected on the basis of the marker. Therefore, when a plurality of semiconductor devices are formed on the semiconductor substrate, it is possible to detect the position of a semiconductor device including the crystal defect.

According to the above-mentioned method, it is possible to easily detect the position of a semiconductor device including the position of a crystal defect on a semiconductor substrate.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

Hereinafter, preferred embodiments of a semiconductor device manufacturing method and a manufacturing device according to the invention will be described in detail with reference to the accompanying drawings.

Embodiments

In the invention, a coordinate origin is formed as a marker on a semiconductor substrate in advance. Therefore, it is possible to determine the position of a crystal defect and the position of a semiconductor device on the basis of the marker and to easily to establish the positional relationship therebetween. A crystal defect detection process can also be included in a semiconductor device manufacturing process.

Figure 1:
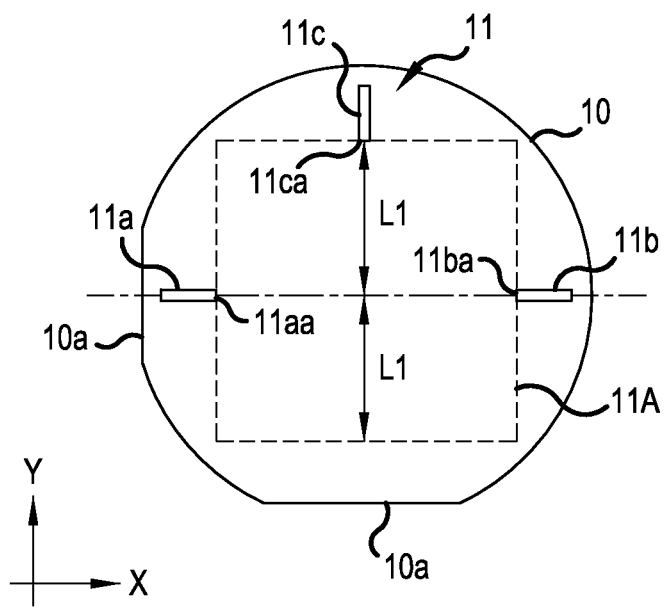
FIG. 1 is a plan view illustrating markers on a semiconductor substrate.

FIG. 1 is a plan view illustrating the markers on the semiconductor substrate. As illustrated in FIG. 1, a plurality of rectangular markers 11 (three rectangular markers in the example illustrated in FIG. 1) are formed on, for example, a SiC substrate 10 as the semiconductor substrate. The markers 11 includes X-axis markers 11a and 11b which are formed at both ends of the SiC substrate 10 along the X-axis so as to be separated from each other, and a Y-axis marker 11c that is provided at one end of the SiC substrate 10 along the Y-axis perpendicular to the X-axis markers 11a and 11b.

A region which is surrounded by two markers 11a and 11b on the X-axis and one marker 11c on the Y-axis can be an in-plane region of the SiC substrate 10. That is, the markers 11 (11a to 11c) are alignment marks which define a plurality of semiconductor device (chip array) manufacturing regions on the SiC substrate 10.

The markers 11 (11a to 11c) can be formed by laser processing on the semiconductor substrate 10. However, the invention is not limited thereto. For example, the markers 11 (11a to 11c) may be formed by photolithography or physical cutting.

In the example illustrated in FIG. 1, the inside of a region which is surrounded by the inner end surfaces 11aa, 11ba, and 11ca of the plurality of markers 11a, 11b, and 11c and is represented by a dotted line in FIG. 1 is a chip array manufacturing region 11A.

Three or more markers 11 are provided at the outer circumferential positions of the SiC substrate 10. Therefore, other devices (for example, an inspection device or a manufacturing device after the markers are formed) can detect three markers 11 using a sensor and define the position of the SiC substrate 10 in the rotation direction, that is, the X-axis position and Y-axis position of each SiC substrate 10. In addition, since the X-axis position and the Y-axis position can be defined, it is possible to detect a plurality of positions in the plane of the SiC substrate 10.

Figure 2:
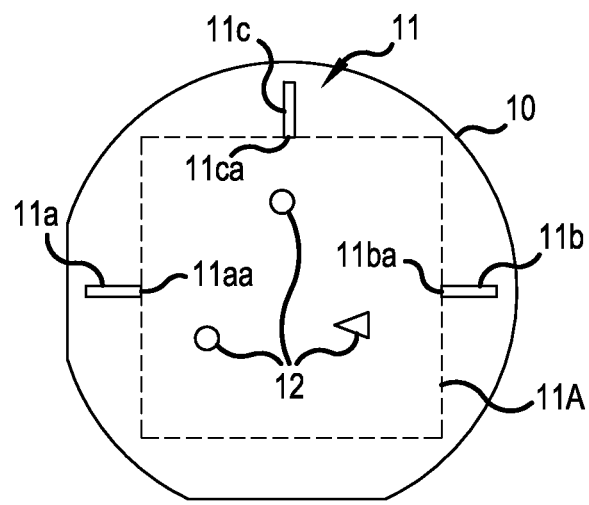
FIG. 2 is a plan view illustrating the position of defects on the semiconductor substrate.

FIG. 2 is a plan view illustrating the position of defects on the semiconductor substrate. The inspection device inspects the SiC substrate 10 on which the markers 11 illustrated in FIG. 1 are formed. The inspection device detects crystal defects 12. The detected crystal defects 12 can be detected as the X-axis and Y-axis coordinate positions of the SiC substrate 10 on the basis of the markers 11 and the positions of the crystal defects 12 which are stored in the inspection device. Marks (identifiers) with a predetermined shape can be attached to the positions of the crystal defects 12 and the images of the marks can be displayed or the marks can be output to the outside. In addition, marks with a shape corresponding to the type of crystal defects 12, for example, a point defect, a line defect, a plane defect, a volume defect, or dislocation may be used, or marks with different shapes, such as ○ and Δ, may be used, as illustrated in FIG. 2.

Figure 3:
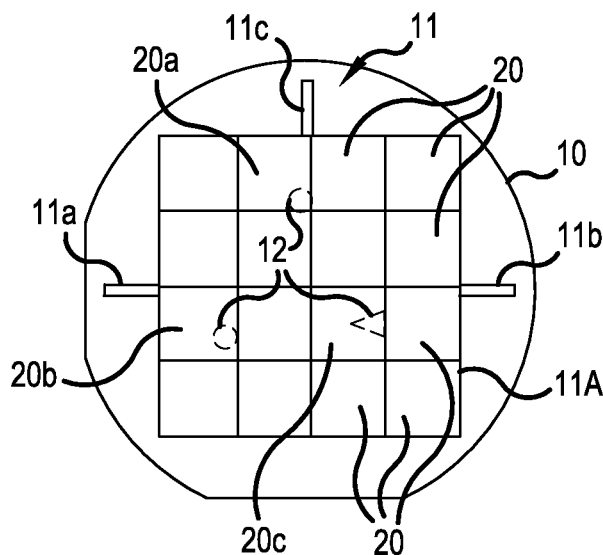
FIG. 3 is a diagram illustrating a chip array manufactured on the semiconductor substrate.

FIG. 3 is a diagram illustrating a chip array which is manufactured on the semiconductor substrate. After the inspection of the SiC substrate by the inspection device illustrated in FIG. 2, the manufacturing device manufactures a plurality of silicon carbide-Schottky barrier diode (SBD) chips 20 in an array shape in the plane of the SiC substrate 10 on the basis of the markers 11 on the SiC substrate 10.

When the manufacturing device manufactures the SBD chips 20, it is possible to determine the regions (coordinate positions) of the SBD chips 20 including the coordinate positions of the crystal defects 12.

Figure 4:
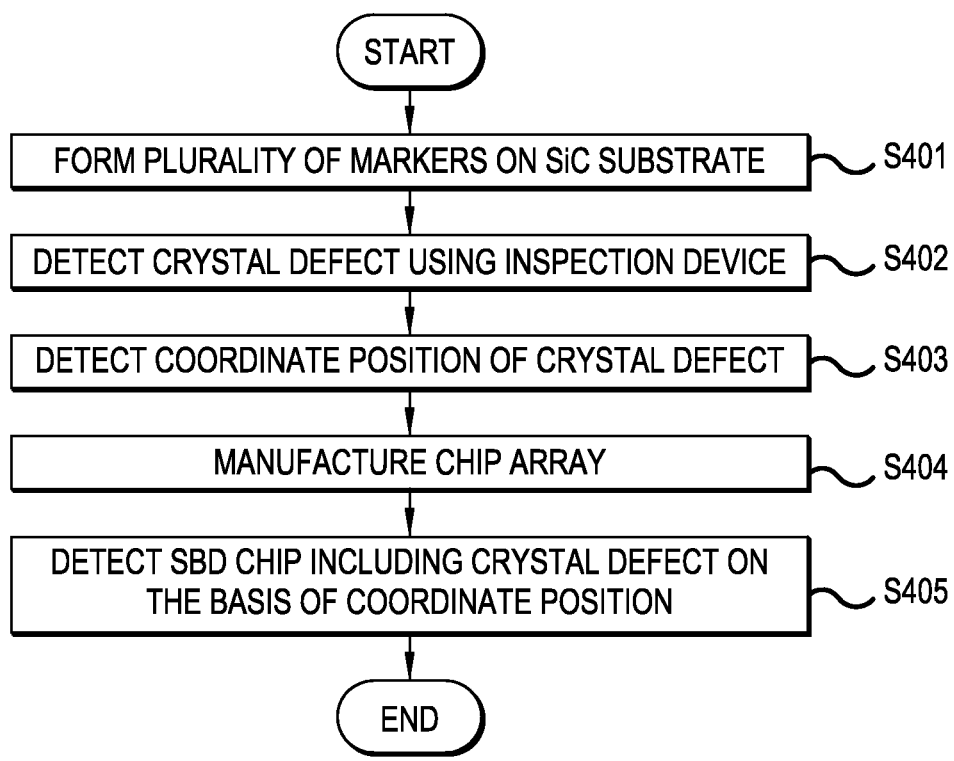
FIG. 4 is a flowchart illustrating an example of a semiconductor substrate manufacturing process.

FIG. 4 is a flowchart illustrating an example of the semiconductor substrate manufacturing process. Next, the formation of the markers, the detection of the crystal defects, and the manufacture of the chip array will be sequentially described with reference to the flowchart. In the following description, it is assumed that the inspection device is incorporated into the manufacturing device and the inspection process is included in one of all manufacturing processes.

As the SiC substrate 10 which is used as the semiconductor substrate, for example, an n-type 4H-SiC single crystal semiconductor substrate is used which has a (0001) plane as the surface, has a diameter of 3 inches, is doped with N (nitrogen), and is 4 degrees off in the <11-20> direction. After chemical mechanical polishing (CMP) is performed on the SiC substrate 10, an n-type epitaxial layer is formed on the surface of the SiC substrate 10. For example, the n-type epitaxial layer has a thickness of 5 μm from the surface and a doping concentration of $1\times10^{16}$ cm$^{-3}$.

As illustrated in FIG. 2, a plurality of rectangular markers 11 which have a length of 300 μm, a width of 50 μm, and a depth of 3 μm are formed on the surface of the SiC substrate 10 by photolithography and etching (Step S401). The markers 11 include the X-axis markers 11a and 11b which are formed at both ends of the SiC substrate 10 along the X-axis so as to be separated from each other and the Y-axis marker 11c which is provided at one end of the SiC substrate 10 along the Y-axis perpendicular to the X-axis markers 11a and 11b.

As described above, the marker 11 may be formed by laser processing or physical cutting. Any method may be used as long as the formed marker 11 can be detected as an alignment for detecting the coordinate position by the sensor.

The X-axis and the Y-axis can be defined on the basis of an orientation flat 10a which is provided on the side of the SiC substrate 10 and the markers 11 (11a to 11c) are formed on the basis of the orientation flat 10a.

Only one Y-axis marker 11c is formed in the upper part of the drawings. A length L1 from a virtual line which connects the X-axis markers 11a and 11b to the Y-axis marker 11c can be detected. Therefore, even though another Y-axis marker is not provided in the lower part of the drawings, the length L1 from the virtual line to a lower boundary line of the chip array manufacturing region 11A can be the same as the length from the virtual line to the Y-axis marker 11c.

Three markers 11 are provided at the outer circumferential positions of the SiC substrate 10. Therefore, other devices can define the position of the SiC substrate 10 in the rotation direction on the basis of the detection positions of the three markers 11, that is, the X-axis position and Y-axis position of each SiC substrate 10. In addition, since the X-axis position and the Y-axis position can be defined, it is possible to detect a plurality of positions in the plane of the SiC substrate 10.

As described above, after the markers 11 are formed on the SiC substrate 10, an inspection unit inspects the SiC substrate 10. During the inspection, the inspection unit detects the markers 11. Then, the inspection unit radiates light and detects crystal defects on the basis of the diffusion, reflection, and transmission of the radiated light. A predetermined method, for example, the electroluminescence method, a method which radiates excitation light to a measurement position to detect crystal defects, or a method which applies a voltage to detect crystal defects may be used in addition to the above-mentioned method (Step S402).

The inspection unit detects the positions (X-axis and Y-axis positions) of the crystal defects 12 in the plane of the SiC substrate 10 on the basis of the markers 11 (Step S403). The positions (X-axis and Y-axis positions) of the detected crystal defects 12 are stored as coordinate positions in a storage unit (not illustrated) of the inspection unit (manufacturing device).

The manufacturing device manufactures a plurality of silicon carbide-Schottky barrier diode (SBD) chips 20 in the plane of the SiC substrate 10 on the basis of the markers 11 (Step S404). The chip array manufacturing region 11A surrounded by the inner end surfaces 11aa, 11ba, and 11ca of the plurality of markers 11a, 11b, and 11c illustrated in FIG. 1 is vertically and horizontally divided into a predetermined number of parts to manufacture the SBD chips 20 illustrated in FIG. 3 in an array shape.

At that time, the manufacturing device detects the SBD chips 20 including the detected crystal defects 12 on the basis of the coordinate positions (Step S405). That is, the SBD chip 20 has a predetermined region which can be indicated by the X and Y coordinates and it is possible to detect the SBD chip 20 including the X and Y coordinates indicating the position of the crystal defect 12. In the example illustrated in FIG. 3, SBD chips 20a, 20b, and 20c include the crystal defects 12. As such, in this embodiment, it is possible to easily detect a semiconductor device (SBD chip 20) including the crystal defect 12 on the semiconductor substrate 10 and the position of the SBD chip 20 including the crystal defect 12.

In the above-mentioned process, the inspection unit is provided in the manufacturing device and the manufacturing device collectively stores the coordinate positions of the crystal defects detected by the inspection unit on the basis of the alignment position defined by the marker 11 while the semiconductor device is being manufactured and uses the coordinate positions for the detection process. However, the invention is not limited thereto. The invention can also be applied to a case in which the manufacturing device and the inspection device are provided at different positions. That is, the position (X-axis and Y-axis positions) of each crystal defect 12 is stored in the storage unit of the inspection device. When the manufacturing device manufactures the SBD chip 20, it reads the position of the crystal defect 12 from the inspection device and can detect the SBD chip 20 including the crystal defect 12. In addition, a mark may be attached to the position of the SBD chip 20 including the crystal defect 12 before the SiC substrate 10 is divided into chips. In this case, after the SiC substrate 10 is divided into chips, it is possible to easily select the SBD chip 20 including the crystal defect 12.

The accuracy of the position of the crystal defect 12 detected by the above-mentioned process will be described. The position of the crystal defect 12 in each SBD chip 20 was actually observed by an optical microscope on the basis of the positional relationship with the marker 11. As a result, the positional deviation was less than about 100 μm. As such, it is possible to accurately detect the position of the crystal defect 12 on the SiC substrate 10 on the basis of the marker 11.

In the above-described embodiment, the markers 11 are formed on the SiC substrate 10 in advance and then the crystal defects 12 are detected. However, the invention is not limited thereto. When the inspection unit detects the crystal defects 12, any method may be used as long as it can detect the coordinate position of each crystal defect 12 on the SiC substrate 10. In addition, the markers 11 may be formed at the same time as the crystal defects 12 are detected or after the crystal defects 12 are detected. The markers 11 may be formed at the same time as the crystal defects 12 are detected and the position of each of the detected crystal defects 12 may be detected on the basis of the position of the markers 11. In addition, when the crystal defects 12 are detected, the coordinate position of each crystal defect 12 may be temporarily determined on the virtual coordinate positions and the marker 11 which is a reference of the temporary coordinate position may be formed.

The above-described embodiment is an illustrative example and the application range of the invention is not limited to the above-described embodiment. For example, the semiconductor substrate is not limited to the SiC substrate, but may be a single crystal substrate such as a gallium nitride (GaN) substrate. In addition, two markers 11 may be provided on each of the X-axis and the Y-axis, or the outer circumference (360 degrees) of the semiconductor substrate may be divided into three equal parts (60 degrees apart) and the markers 11 may be provided in the divided parts.

INDUSTRIAL APPLICABILITY

As described above, the semiconductor device manufacturing method and the manufacturing device according to the invention are useful for power semiconductor devices which are used in, for example, inverters of industrial electric motors or Shinkansen trains that require a large amount of current.

Thus, a semiconductor has been described according to the present invention. Many modifications and variations may be made to the techniques and structures described and illustrated herein without departing from the spirit and scope of the invention. Accordingly, it should be understood that the devices and methods described herein are illustrative only and are not limiting upon the scope of the invention.

EXPLANATIONS OF LETTERS OR NUMERALS

10 Semiconductor Substrate (SiC substrate)
11 (11a, 11b, 11c) Marker
12 Crystal Defect
20 SBD Chip

What is claimed is:
1. A semiconductor device manufacturing method comprising:
a step of forming a marker which is a reference for a coordinate position defining a region of a chip that is manufactured in a semiconductor substrate;
a step of detecting a crystal defect on the semiconductor substrate;
a step of obtaining a coordinate position of the detected crystal defect relative to the coordinate position of the marker; and
a step of, when a plurality of semiconductor devices are manufactured on the semiconductor substrate, detecting a semiconductor device including the crystal defect among the plurality of semiconductor devices, on the basis of the coordinate position wherein the marker is formed after the crystal defect is detected.

2. The semiconductor device manufacturing method according to claim 1, wherein the semiconductor substrate is made of silicon carbide.

3. The semiconductor device manufacturing method according to claim 1, wherein the semiconductor substrate is made of gallium nitride.

4. The semiconductor device manufacturing method according to claim 1, wherein the marker is formed by laser.

5. The semiconductor device manufacturing method according to claim 1, wherein the marker is formed by photolithography.

6. The semiconductor device manufacturing method according to claim 1, wherein the marker is formed by physical cutting.

7. The semiconductor device manufacturing method according to claim 1, wherein light is radiated to the semiconductor substrate and the crystal defect is detected on the basis of the diffusion, reflection, and transmission of the radiated light.

8. The semiconductor device manufacturing method according to claim 1, wherein coordinate positions of detected crystal defect are stored in a storage unit.

9. A semiconductor device manufacturing method comprising:

a step of forming a marker which is a reference for a coordinate position defining a region of a chip that is manufactured in a semiconductor substrate;

a step of detecting a crystal defect on the semiconductor substrate; and a step of obtaining a coordinate position of the detected crystal defect relative to the coordinate position of the marker, wherein the marker is formed at the same time as the crystal defect is detected.

10. A semiconductor device manufacturing method comprising:

a step of forming a marker which is a reference for a coordinate position defining a region of a chip that is manufactured in a semiconductor substrate;

a step of detecting a crystal defect on the semiconductor substrate;

a step of obtaining a coordinate position of the detected crystal defect relative to the coordinate position of the marker; and a step of, when a plurality of semiconductor devices are manufactured on the semiconductor substrate, detecting a semiconductor device including the crystal defect among the plurality of the semiconductor devices, on the basis of the coordinate position, wherein the marker comprises two markers on a first coordinate axis and one marker on a second coordinate axis.

* * * * *